(12) United States Patent
Kaplan

(10) Patent No.: US 8,077,914 B1
(45) Date of Patent: Dec. 13, 2011

(54) OPTICAL TRACKING APPARATUS USING SIX DEGREES OF FREEDOM

(76) Inventor: Arkady Kaplan, Rockville, MD (US)

(*) Notice: Subject to any disclaimer, the term of this patent is extended or adjusted under 35 U.S.C. 154(b) by 1162 days.

(21) Appl. No.: 11/835,002

(22) Filed: Aug. 7, 2007

Related U.S. Application Data

(60) Provisional application No. 60/835,874, filed on Aug. 7, 2006.

(51) Int. Cl.
*G06K 9/00* (2006.01)
*A61B 3/14* (2006.01)

(52) U.S. Cl. ........................ 382/103; 351/209

(58) Field of Classification Search ............ 382/103
See application file for complete search history.

(56) References Cited

U.S. PATENT DOCUMENTS

| | | | | |
|---|---|---|---|---|
| 4,103,435 | A * | 8/1978 | Herndon | 434/43 |
| 4,973,149 | A | 11/1990 | Hutchinson | |
| 5,231,674 | A * | 7/1993 | Cleveland et al. | 382/117 |
| 5,604,818 | A | 2/1997 | Saitou | |
| 5,686,942 | A | 11/1997 | Ball | |
| 6,152,563 | A | 11/2000 | Hutchinson | |
| 6,578,962 | B1 * | 6/2003 | Amir et al. | 351/209 |
| 6,659,611 | B2 * | 12/2003 | Amir et al. | 351/210 |
| 7,206,435 | B2 | 4/2007 | Fujimura | |
| 2004/0174496 | A1 * | 9/2004 | Ji et al. | 351/209 |
| 2004/0252277 | A1 * | 12/2004 | Chmielewski et al. | 351/209 |
| 2005/0175218 | A1 * | 8/2005 | Vertegaal et al. | 382/103 |
| 2006/0110008 | A1 * | 5/2006 | Vertegaal et al. | 382/103 |
| 2006/0210122 | A1 * | 9/2006 | Cleveland et al. | 382/117 |
| 2006/0239670 | A1 * | 10/2006 | Cleveland | 396/51 |
| 2007/0081695 | A1 * | 4/2007 | Foxlin et al. | 382/103 |

OTHER PUBLICATIONS

Shih et al., A Calibration-Free Gaze Tracking Technique, Pattern Recognition, 2000. Proceedings. 15th International Conference on, vol. 4, pp. 201-204, 2000.*
Morimoto et al., Pupil detection and tracking using multiple light sources, Image and Visuion Computing, vol. 18, 2000, pp. 331-335.*
M. Böhme et al, "Remote Eye Tracking: State of the Art and Directions for Future Development," COGAIN 2006: Gazing into the Future, Turin, Italy, 2006, pp. 1-5.
C. H. Morimoto et al, "Pupil Detection and Tracking Using Multiple Light Sources", Image and Vision Computing, vol. 18, No. 4, 2000, pp. 331-336.

(Continued)

*Primary Examiner* — David Zarka
(74) *Attorney, Agent, or Firm* — Nadya Reingand

(57) ABSTRACT

This invention discloses an optical object tracking method and system with to up to six degrees of freedom: three translational and three angular coordinates. In the preferred embodiment, the system includes two near-infra-red light sources (e.g., light emitting diode), two cameras, and a digital signal processor. The system performs to tasks: object locking and tracking. For object locking and tracking, a single camera and two off-axis light sources are engaged. For more precise object tracking, two spatially-separate cameras and a single diode are used. In another embodiment, a third camera may be used to separate the locking and tracking tasks. The light sources may have different light wavelengths and may operate in a sequential mode. The cameras may be sensitive over different spectral ranges and may also differ in terms of field-of-view and resolution. The invention describes a method based on capturing images of light reflections at the camera focal plane and analyzing them, through mathematical mapping, for known locations of light sources and cameras. Invention can be adopted for the tracking of an eyeball. The related method determines an object location and orientation or a gaze vector and a point-of-regard.

19 Claims, 10 Drawing Sheets

OTHER PUBLICATIONS

G. Hennessey et al, "Single camera Eye-Gaze Tracking System with Free Head Motion", ETRA 2006, pp. 87-94.
A. Haro et al, "Detecting and Tracking Eyes by using their Physiological Properties, Dynamics, and Appearance". Proceedings of CVPR, 2000, pp. 163-168.
S. W. Shih et al, "A Calibration-Free Gaze Tracking Technique", In Proceedings of the International Conference on Pattern Recognition (ICPR'00), 2000, pp. 201-204.
A. Tomono et al, "A TV camera system which extracts feature points for non-contact eye movement detection", SPIE Proceedings, vol. 1194, 1989, pp. 2-12.
Y. Matsumoto et al, "An Algorithm for Real-time Stereo Vision Implementation of Head Pose and Gaze Direction Measurement", IEEE Proceedings of 4th ICAFGR, 2000, pp. 499-504.
T. Ohno, et al, "Just Blink Your Eyes: A Head-Free Gaze Tracking System", Proceedings of CHI2003, 2003, pp. 950-951.

* cited by examiner 103, 104, 301

103, 104, 301

OPTICAL TRACKING APPARATUS USING SIX DEGREES OF FREEDOM

RELATED APPLICATIONS

This application claims benefit of the U.S. provisional patent application No. 60/835,874 filed Aug. 7, 2006.

FIELD OF THE INVENTION

The invention relates generally to an apparatus and method for real-time multi-degree of freedom (DoF) optical tracking, which determines the location of an object with a single camera and further performs precise tracking of the object by a pair of cameras. More particularly, invention relates to eye tracking and determines a point of gaze (line of sight).

BACKGROUND OF THE INVENTION

Optical motion capture systems are typically based on high contrast video imaging of retro-reflective markers, which are attached to strategic locations on an object. The markers are usually spherical objects or disks ranging from 1 to 5 cm in diameter, depending on the motion capture hardware and the size of the active area, and are sometimes covered by reflective materials. Some markers may incorporate infra-red (IR) light emitting diodes (LEDs) to enhance contrast. The number, size, shape, and placement of markers depend on the type of motion to be captured and desired quality (accuracy). In many applications, multi DoF measurements are required. For instance, in addition to three position coordinates, the angular orientation of an object may also need to be calculated. Usually, in these cases a rigid combination of several markers, called a "rigid body" is used for tracking. Obtaining more detailed rotational information always requires additional markers. Additional markers can also provide redundancy and overcome occlusion problems.

In conventional optical trackers, each marker is tracked by an array of high-resolution high-speed digital cameras that cover a working area. The number of cameras depends on the type of motion capture. To enhance the contrast, each camera is equipped with IR LEDs and IR pass filters over the camera lens. Appropriate software receives the 2D coordinates of markers, as captured by the tracking cameras, and calculates the positions of individual markers (3 DoF) or rigid bodies (6 DoF). Adding more cameras helps alleviate performance issues, but further drives up the system complexity and cost.

Optical tracking can be applied to tracking eye movements and measure (compute) the gaze direction of a person who is looking at a particular point in space or on a display. However, these measurements are difficult to achieve in practice and require high-precision instruments as well as sophisticated data analysis and interpretation. Over the years, a variety of eye-gaze (eye-movement) tracking techniques have been developed, such as Purkinje Image Tracking, Limbus, Pupil, Eyelid Tracking, Cornea and Pupil Reflection Relationship (see, for example "Remote Eye Tracking: State of the Art and Directions for Future Development", The 2nd Conference on Communication by Gaze Interaction—COGAIN 2006: Gazing into the Future, pp. 1-5, Sep. 4-5, 2006, Turin, Italy by M. Böhme et al). Despite the number of developed techniques, the concomitant improvement in performance has been rather modest. Developers are still being challenged by problems related to head-movement, tracker over-sensitivity and/or unreliable calibration. Some systems require complicated personal calibration procedures, others are based on wearable head-mounted gears, and some restrict the user's head positions within a narrow area. Every remote eye-tracking system (i.e. when no head-mounted gear is used) has its own problem of head movement compensation, which must be addressed appropriately. For example, a small 2D mark may be attached to the head or a cap on it and used, as a reference, in order to compensate for head movement. The use of nose-feature image extraction as a reference point has also been explored, see, for example, U.S. Pat. No. 5,686,942 by Ball. And so has been a hybrid approach to head movement compensation that entailed a combination of optical eye-tracking and magnetic or ultrasound trackers. The drawbacks of these approaches are the need for a separate control unit and the use of bulky transmitters. In sum, there is still an urgent need for an accurate, unobtrusive, and reliable method and system of real-time gaze-tracking.

Currently, the most promising approach is the near-infrared reflection (NIRM) two-point optical gaze-tracking method. It requires no mounted equipment and allows for small head motions. The tolerance to insignificant head movements is gained by tracking two reflection points (glints) of the eye and distinguishing head movements (points move together without changing their relative position) from eye movements (points move with respect of one another). One of the most common variations of the NIRM gaze-tracking method employs pupil and Purkinje image processing and is a relatively accurate gaze tracking technique (see, for example, "Pupil Detection and Tracking Using Multiple Light Sources", Image and Vision Computing, Volume: 18, No. 4, pp. 331-336, 2000 by C. H. Morimoto et al; also "Single camera Eye-Gaze Tracking System with Free Head Motion", ETRA 2006, pp. 87-94 by G. Hennessey et al.; also U.S. Pat. Nos. 5,604,818 by Saitou, 4,973,149 by Hutchinson, and 6,152,563 by Hutchinson). This method is frequently employed in advanced research and commercial products.

Much effort has been dedicated to NIRM-based tracking in an attempt to improve its robustness, mitigate the head-movement problem, and simplify calibration. In particular, physiological aspects and appearance of eyes as well as head/eye motion dynamics were analyzed in "Detecting and Tracking Eyes by using their Physiological Properties, Dynamics, and Appearance", Proceedings of CVPR, pp. 163-168, 2000 by A. Haro et al., The use of multiple cameras and light sources has also been considered in "A Calibration-Free Gaze Tracking Technique", In Proceedings of the International Conference on Pattern Recognition (ICPR'00), pp. 201-204, 2000 by S. W. Shih et al., A real-time imaging system reported in "A TV camera system which extracts feature points for non-contact eye movement detection", In Proceedings of the SPIE Optics, Illumination, and Image Sensing for Machine Vision IV, Vol. 1194, pp. 2-12, 1989 by A. Tomono et al. comprised three CCD cameras and two NIR light sources at two wavelengths, one of which was polarized. The system implemented a combined differencing and threshold and allowed for pupil and corneal reflection segmentation by using different CCD sensitivity and polarization filtering. A relatively robust method for gaze direction detection was realized by combining a real-time stereovision technique (to measure head position) with limbus detection (the boundary between a bright sclera and a dark iris), see "An Algorithm for Real-time Stereo Vision Implementation of Head Pose and Gaze Direction Measurement", In Proceedings of Fourth IEEE International Conference on Automatic Face and Gesture Recognition, pp. 499-504, 2000 by Y. Matsumoto et al. However, this method suffered from a low angular resolution and compromised accuracy. In "Just Blink Your Eyes: A Head-Free Gaze Tracking System", Proceedings of CHI2003, pp. 950-951, 2003 by T. Ohno et al., a stereo imaging unit (two CCD cameras) for determining eye positioning was complemented by a conventional gaze tracking imaging unit for detecting the pupil and corneal reflection (Purkinje image). As yet another example of prior art, U.S. Pat. No. 7,206,435 by Fujimura et al, discloses a combination of bright and dark pupil images by implementing two spatially separate light-emitting diode arrays (rings); one around the camera lens and another far from the lens. While the robustness of pupil tracking may be improved with this implementation, the problem of head movement compensation remains unresolved.

Since the NIRM invokes the use of illumination, several studies have attempted to optimize its use. It is known that when an on-axis light source is used (i.e. it is positioned coaxially with the camera optical axis), the pupil appears bright because the light reflected from the eye interior is able to reach the camera. On the contrary, illumination by an off-axis source generates a dark pupil image. Commercial remote eye tracking systems mostly rely on a single light source positioned either off-axis or on-axis (point or ring-type). Examples are presented by eye trackers made by ISCAN Incorporated from Burlington, Mass.; LC Technologies from McLean, Va.; ASL from Bedford, Mass. Some other approaches employ multiple cameras with multiple on-axis light sources and attempt to estimate the line of sight without using any of the user-dependent parameters ('calibration free'), see, for example, U.S. Pat. No. 6,659,611 by Amir et al. and "A Calibration-Free Gaze Tracking Technique", in Proceedings of the International Conference on Pattern Recognition (ICPR'00), pp. 201-204, 2000 by S. W. Shih et al.

It is worthwhile to note that despite the obvious advantages of using bright pupil conditions, this type of illumination inherently limits tracking resolution due to a relatively high sensitivity to head movements. It is especially true when speaking of head movements along the line of sight. Another NIRM based approach invokes the use of two optical point sources for simultaneous eye position and gaze detection, as disclosed in U.S. Pat. No. 5,604,818 Saitou et al. and in "Single camera Eye-Gaze Tracking System with Free Head Motion", ETRA 2006, pp. 87-94 by G. Hennessey et al. However, the accuracy of this approach is compromised in cases when glints are located close to the optical axis (i.e. the straight line connecting the origin (camera) and object (cornea center)). In these cases, the error is proportional to the square of the angle between the optical axis and the direction to the glints. Thus, the error increases rapidly with the distance between glints.

While the aforementioned prior art methods are useful advances in the field of eye-gaze tracking, they are adversely affected by short tracking ranges, frequent recalibration, flow stability (frequent floss of tracking) and high cost. All these deficiencies prevent object/eye trackers from being used by the general public and limit their applications to research laboratories and boutique markets.

In light of the above review of prior art, there is an apparent need for a unobtrusive optical tracking method that is robust under various light conditions and stable within a wider range of tracking. Such a method should obviate recalibration and have high speed and good angular resolution within an extended range of tracking. Finally, the method should lend itself to making an inexpensive optical tracking device suitable for mass production.

SUMMARY OF THE INVENTION

The present invention discloses an apparatus and method for real-time optical tracking with multi degrees of freedom (DoF). In one preferred embodiment, a single camera determines the location of an object of regard illuminated by two light sources, which is then illuminated only by a single source and precisely tracked by a pair of cameras. Real-time detection and tracking of an object with up to six DoF: three linear dimensions and three angular orientations is accomplished by mapping calculations for known relative distances between cameras and sources as well as equations modeling the object's three-dimensional surface. Optical tracking with additional DoFs, i.e. rotational movements (yaw/pitch/roll), may be needed and enabled for either non-spherical objects or objects with surface mark(s) of a known (or predictable) shape, distinctive reflection and, optionally, emitting light. The present invention addresses both these cases.

One embodiment of the present invention, called hereinafter a first operational mode, invokes more than one off-axis light source in combination with a single camera. The use of at least two glint spots produced by multiple light sources and detected by a single camera significantly improves the robustness of object locking and tracking. A second operational mode employs two cameras and a single off-axis light source, while the other light sources are blocked or switched off. Two glint spots are produced by the same optical source and each spot is detected only by one corresponding camera. This mode enables more accurate object locking and tracking.

One preferred embodiment comprises two off-axis optical sources and two cameras and performs the two operational modes cyclically, i.e. one after another. In yet another embodiment, an additional camera is included to enable performing the two operational modes concurrently. The cameras may have different fields of view and/or discriminative sensitivity with respect to the light sources, which may differ from each other.

The system may also be applied to eye ball location and orientation tracking and computing a gaze direction (line of sight) in real time. For this purpose, eye features, such as a subject's pupil are treated as object surface marks and used for multi DoF tracking. In yet another embodiment, the cameras may have additional on-axis illumination to intensify the appearance of the pupils.

BRIEF DESCRIPTION OF THE DRAWINGS

FIG. 1 schematically illustrates one preferred embodiment, which includes light sources, imaging devices and object.

FIG. 6 illustrates the principle of optical tracking.

DETAILED DESCRIPTION OF THE PREFERRED EMBODIMENT

The present invention is now described more fully with reference to the accompanying figures, in which some of all possible embodiments of the invention are shown. The present invention may be embodied in various forms and should not be viewed as limited to the embodiments set forth herein. Rather these embodiments are provided so that this disclosure will be thorough and complete and will fully disclose the invention to those skilled in the art.

Figure 1A:
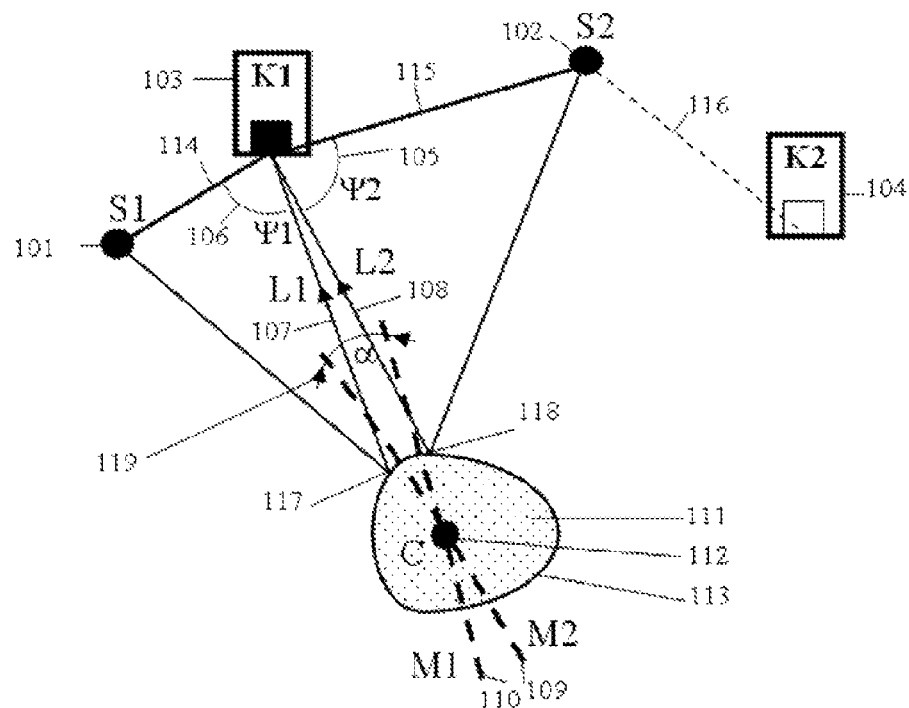
FIG. 1A shows the first operational mode.
Figure 1B:
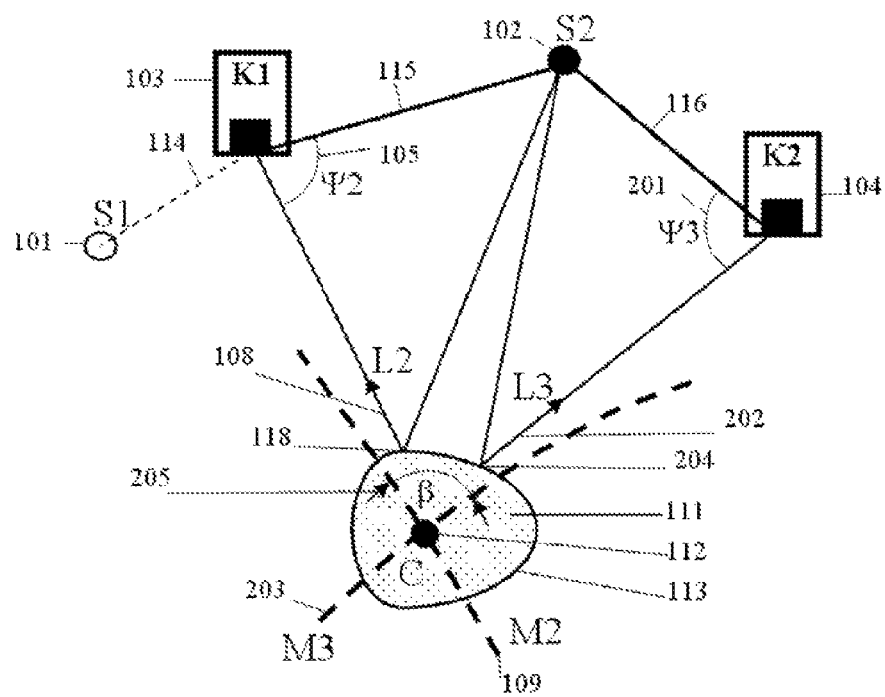
FIG. 1B shows the second operational mode.

One preferred embodiment of the invention consists of two off-axis optical sources S1 and S2 and two cameras K1 and K2, as shown in FIG. 1A and FIG. 1B. Such an embodiment is capable of performing the two operational modes in cycles, i.e. one after another. Accordingly, the first operational mode is shown schematically in FIG. 1A, while the second operational mode in FIG. 1B.

FIG. 1 represents the following elements of the preferred embodiment: S1 and S1 are a first and second light source (101 and 102), respectively; K1 and K2 are a first and second camera (103 and 104), respectively; (111) is an object of regard with its surface (for example, an eye cornea) (113) and its geometrical center (112). The light beams impingent on the object from light sources S1 (101) and S2 (102) are reflected from the object surface towards camera K1 (103). The surface reflection spots from light sources S1 (101) and S2 (102) are glints (117) and (118), respectively. L1 (107) and L2 (108) are the vectors defining the mutual glint-camera directions (117)-(103) and (118)-(103), which correspond to the reflections from light sources S1 (101) and S2 (102) towards camera K (103).

As stated above, this embodiment enables two operational modes. Which mode is activated depends on how exactly the components are engaged in object locking and tracking. The first operational mode is illustrated in FIG. 1A and uses two glint spots (117 and 118) from two off-axis light sources S1 (101) and S2 (102). The spots are imaged by a single camera K1 (103). While the first operational mode provides reliable and fast object locking, it may suffer from low stability and tracking robustness as well as a loss of calibration, especially at long distances.

The second operational mode is shown in FIG. 1B and involves two cameras K1 and K2 (103 and 104) and a single off-axis light source S2 (102). This mode uses two glint spots (118 and 204), each of them being imaged by its corresponding camera only. For this configuration, there is another surface-reflection-spot (glint 204), which is caused by light source S2 (102). Vector L3 (202) defines the mutual glint-camera direction (204)-(104), which corresponds to the reflection from light source S2 (102) to camera K2. The second operational mode provides more accurate object locking and tracking, in particular over wider tracking ranges (at longer distances). It is important to note that light source S2 (102) is used in both operational modes, while light, source S1 (101) only in the first operational mode, since S1 is switched off (blocked) during the second operational mode.

M1 (110) is the curve defining a possible location of the object's geometrical center (for example, a cornea center) for the glint (117) located on the line defined by vector L1 (107). M2 (109) is the curve defining a possible location of the object's geometrical center (cornea center) for the glint (118) located on the line defined by vector L2 (108). M3 (203) is the curve defining a possible location of the object's geometrical center (cornea center) for the glint (204) located on the line defined by vector L3 (202). If the object surface is described by a known equation, curves M1 (110), M2 (109), and M3 (203) can be determined algorithmically using vectors normal to the object surface at the glint points (117), (118) and (204), respectively.

The crossing point of curves M1 (110) and M2 (109) uniquely determines the geometrical location of the object for the first operational mode, i.e. when one camera K1 (103) and two light sources, S1 (101) and S2 (102), are engaged. The crossing point of curves M2 (110) and M3 (203) uniquely determines the geometrical location of the object for the second operational mode, i.e. when two cameras, K1 (103) and K2 (104), and one light source S2 (102) are engaged. As can be seen, the angle $\alpha$ (119) between the crossing curves M1 (110) and M2 (109) in the first operational mode is much smaller than the angle $\beta$ (205) between the crossing curves M2 (109) and M3 (203) in the second operational mode of operation, i.e. $\alpha \ll \beta$. For example, in the preferred embodiment, the $\alpha/\beta$ ratio can be equal to $1/10$.

As a result, the relative accuracy of tracking of the object center is lower for the first operational mode than the second operational mode. For example, in the preferred embodiment, the accuracy of the object center detection in the first operation mode is 4 mm and 1 mm for the first and the second operation mode, respectively. Consequently, in case of the eye-tracking preferred embodiment the difference in accuracy of the object center detection may lead to 1 degree of the visual angle accuracy versus 0.4 degree of the visual angle accuracy, for the first and second operation mode, respectively.

However, the first operational mode identifies glints with more reliability and simplicity, since the directions L1 (107) and L2 (108) to the closely spaced glints (117) and (118) provide an immediate approximate location of the object's center. Thus, there is an optimum mode of operation, which combines the first and second operational modes. The first operational mode may be used to initially locate an object of regard as well as lock on it. The second operational mode receives locking data from the first operational mode and subsequently uses it to provide accurate locking and tracking. The object data obtained by either operational mode can be used by the other operational mode.

Combining the two operational modes enables robust and reliable tracking, which is less sensitive to variations in ambient light and maintains accuracy over a wider tracking range. The disclosed combination of the two operational modes can be synchronized electronically with a frame ratio A/B, where A and B are the number of frames obtained during the first and second operational mode, respectively. For example, in the preferred embodiment, the A/B ratio can be equal to $1/10$.

Figure 2:
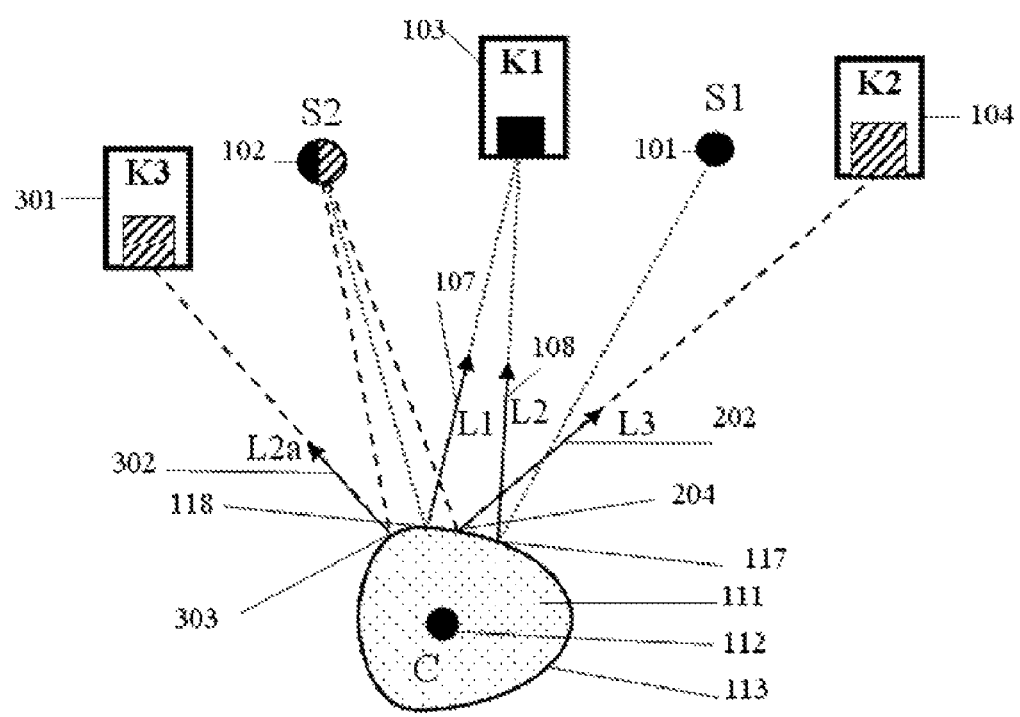
FIG. 2 illustrates an alternative tracking configuration with an additional camera.

Alternatively, the two operational modes may be implemented in such a way as to allow them to operate independently and simultaneously, as illustrated by FIG. 2. In this embodiment, the first operational mode uses, as disclosed above, one camera K1 (103) and two light sources, S1 (101) and S2 (102). The second operational mode employs two cameras, K3 (103) and K2 (104), and a single light source S1 (102). Source S1 (102) is used simultaneously in both operational modes. Vector L2a (302) in FIG. 2 is analogous to vector L2 (108) in FIG. 1 and defines the mutual glint-camera direction (303)-(301) that corresponds to reflections from light source S1 (101) towards camera K3 (301). Vector L3 (202) defines the mutual glint-camera direction (204)-(104) that corresponds to reflection from light source 52 (102) to camera K2 (104). In the configuration of FIG. 2, vectors L2 and L3 are used for the second operational mode, while vectors L1 and L2 for the first operational mode. Thus, in this embodiment the two operational modes can function independently and simultaneously.

Figure 3A:
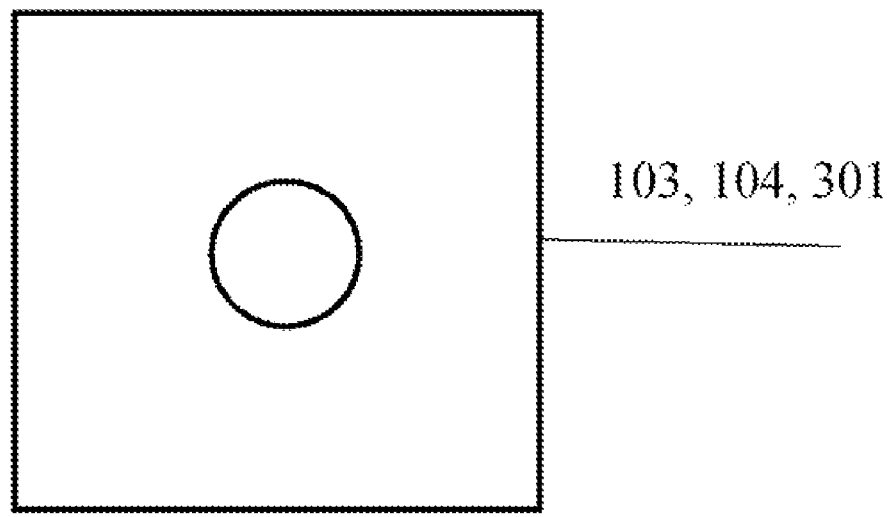
FIG. 3 depicts a preferred imaging device (camera) without on-axis illumination (FIG. 3A) and with on-axis illumination (FIG. 3B).
Figure 3B:
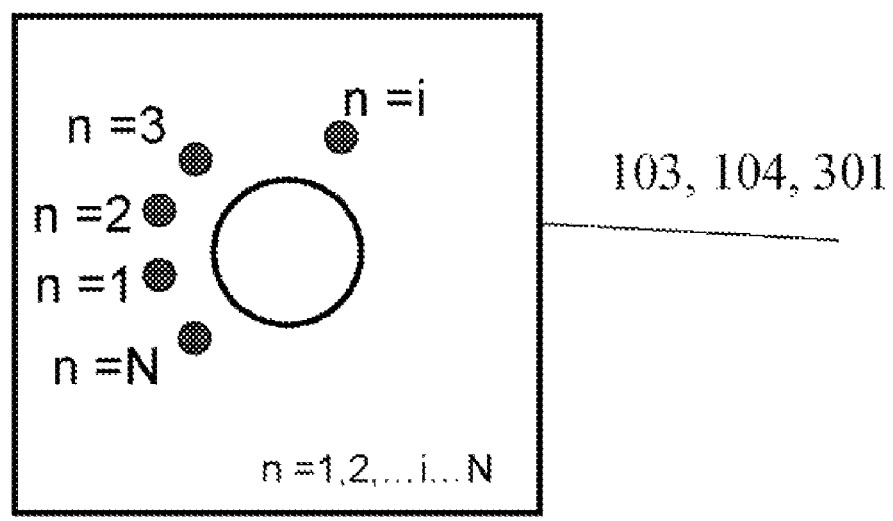

FIG. 3A illustrates a preferred configuration of an imaging device (camera) in accordance with the present invention. In FIG. 3A, the circle represents the camera lens. An alternative embodiment illustrated in FIG. 3B includes a plurality of preferably infra-red light emitting diodes (black dots) which are positioned sufficiently close to the optical axis of the camera lens (circle) so as to produce a bright pupil image for eyeball tracking. The lens of the camera is generally focused on the subject. For eyeball center tracking (described below in detail), the first and second light sources S1 (101) and S2 (102) are positioned sufficiently far from the optical axis of the camera lens so as to produce a dark pupil image. The camera focal distance or the object-to-camera distance may vary depending on the application and be adjusted accordingly. In one embodiment of the present invention, the camera may be equipped with objective lenses to adjust the subject's image.

Figure 4A:
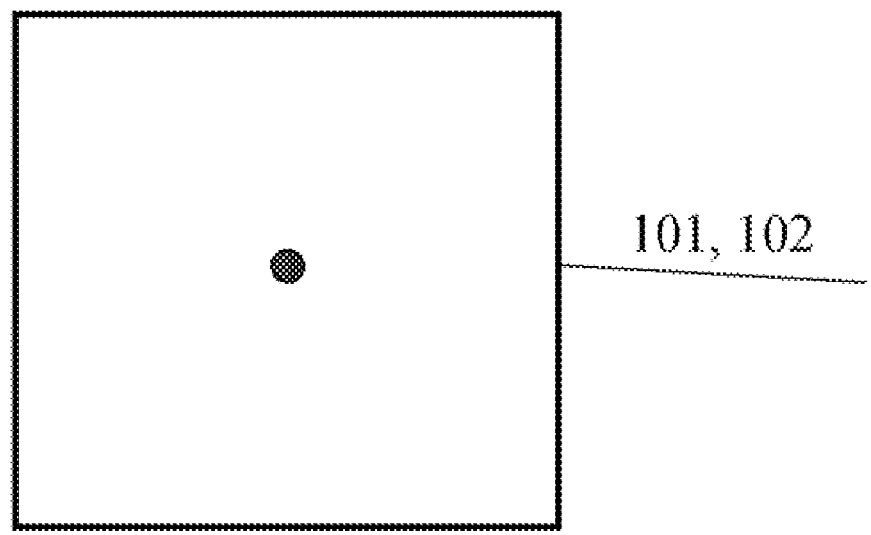
FIG. 4 depicts a preferred light source, based on a single emitting light source (FIG. 4A) or an array of emitting light sources (FIG. 4B).
Figure 4B:
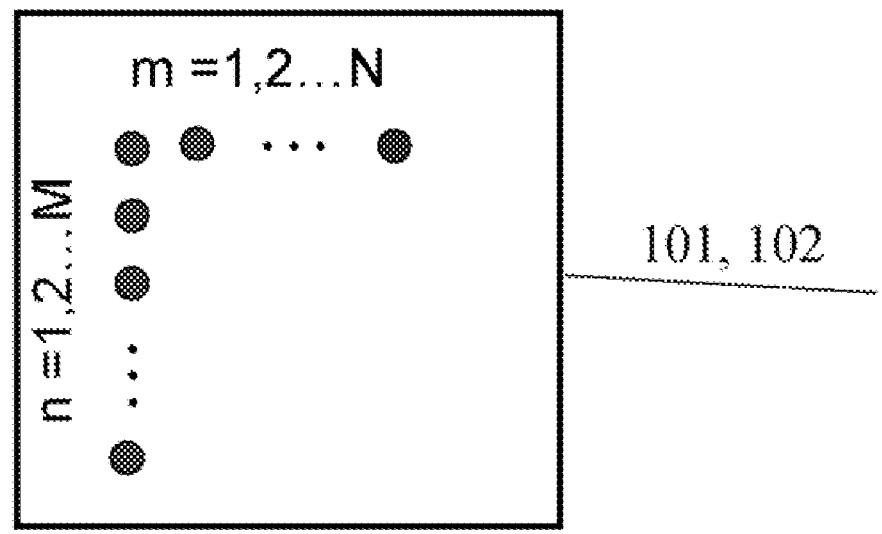

FIG. 4A illustrates a preferred configuration of light sources S1 (101) and S2 (102) in accordance with the present invention. In FIG. 4A, the black dot denotes a single light source, e.g., an infra-red light emitting diode. An alternative embodiment is illustrated in FIG. 4B and includes a plurality of preferably infra-red light emitting diodes, which may be arranged in a certain configuration, such as a one-dimensional or two-dimensional array, depending on the application. For eyeball tracking (described below in detail), light sources S1 and S2 (101) and (102) are positioned off the optical axes of cameras (103), (104) and (301) and produce a dark pupil image.

Figure 5A:
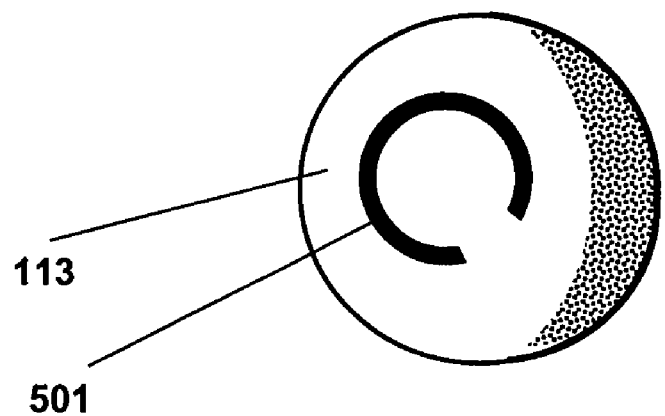
FIG. 5 provides examples of passive markers as objects for 6-DoF (FIG. 5A) and 5-DoF optical tracking (FIG. 5B).
Figure 5B:
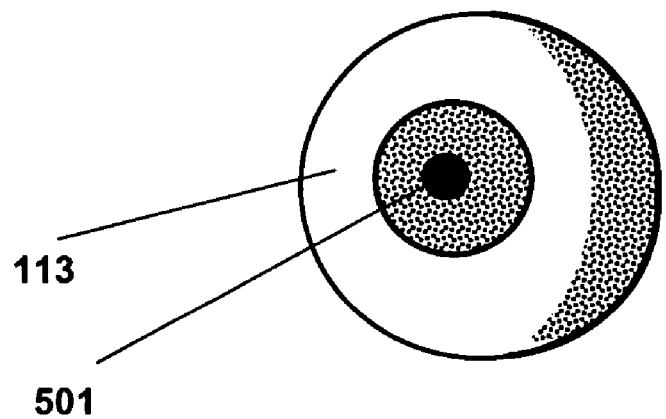

FIG. 5A and FIG. 5B exemplify various objects, including a human eye prosthesis (in FIG. 5B), which were used for multi-dimensional DoF optical tracking by preferred embodiments of the invention and will be further discussed.

Even in a minimal configuration, i.e., in the first operational mode (see FIG. 1A), with a single camera and two light sources, the disclosed method ensures that eye-gaze tracking does not strongly depend on user-specific parameters. Studies showed that only small errors are caused by individual differences in the cornea radius and the pupil size (illumination changes). This must be taken into account, but the user is free of recalibrations caused by changes in the head position and related calibration errors. The tracking procedure and algorithm are described below mostly for the first operational mode. Those skilled in the art will appreciate that the same method can be fully extended to the second operational mode of the invention.

The light sources (101) and (102) may have different wavelengths, while the cameras (103), (104), and (301) are sensitive over different spectral ranges. The wavelength of light may be optimized so as to make the fovea of the eye resolvable. In one embodiment, a source of deep blue or violet light, which is partially reflected and partially absorbed by the retina, may be used in conjunction with a narrow FOV camera. The cameras (103), (104), and (301) may also differ in terms of field-of-view (FOV) and resolution. For example, one camera with a narrower FOV and higher resolution may be implemented to capture and analyze images of at least one object in a scene provided by another camera (with a wider FOV and lower resolution). The latter provides initial information about the object location for the higher-resolution narrow FOV camera.

The invention may be adapted for remote tracking of various objects, including human or animal eye features, where on-axis lighting may be used to intensify the appearance of the subject's pupils. Embodiments of the present invention may also use dark pupil images in combination with bright pupil images in order to improve the pupil detection by emphasizing the contrast of pupil edges. By making head movement measurements an integral part of the system's operation, a calibration procedure may be simplified or eliminated.

A. Object Center Tracking

Figure 6A:
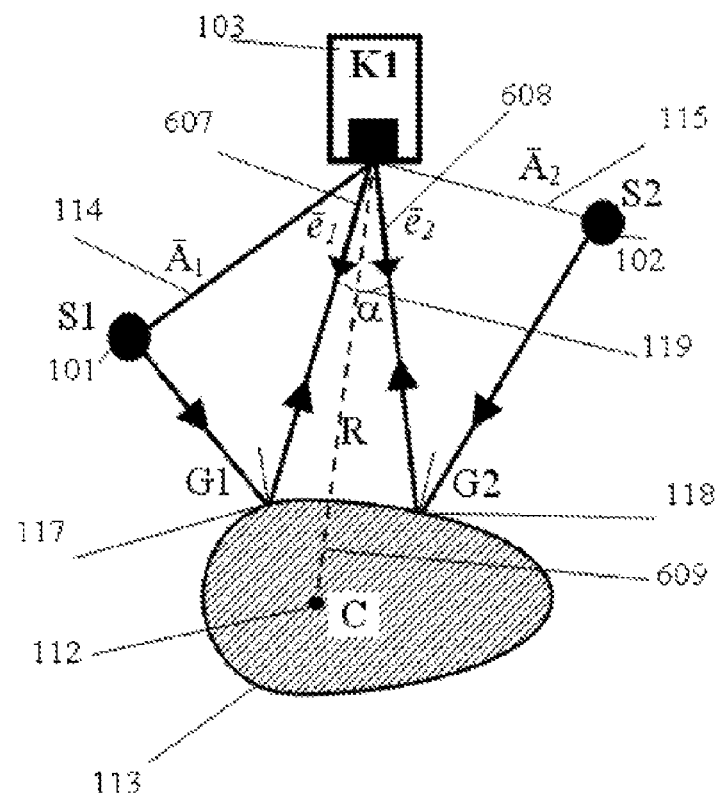
FIG. 6A and FIG. 6B show parameters used by the tracking procedure.

The present invention may be implemented using a real-time measurement of 3-dimensional unit vectors $\{\tilde{e}\}$, which define the directions between a camera (coordinate origin) and reflected images from point sources (i.e. glints at the object surface). FIG. 6A illustrates an optical tracking scheme for the simplest case of a single camera (103) and two sources S1 (101) and S2 (102) where the unit vectors (607), (608) are denoted as $\tilde{e}_1$ and $\tilde{e}_2$. The two glints G1 (117) and G2 (118) produced by point sources at the object surface are shown in FIG. 6A. This drawing corresponds to the first operational mode but is valid for the second operation mode as well.

Figure 6B:
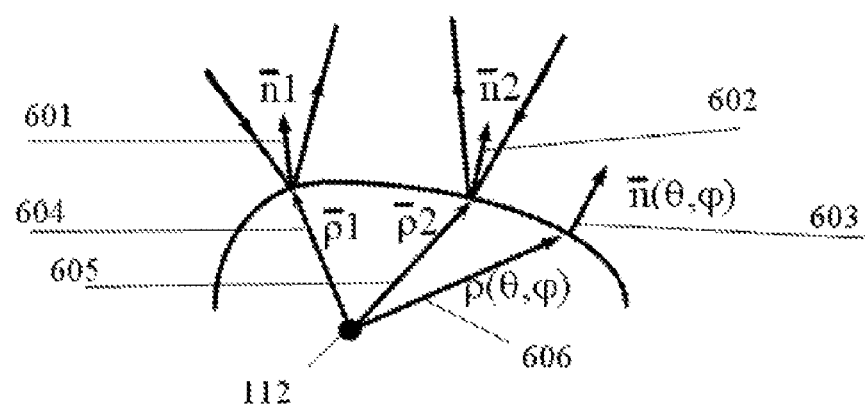

Shown in FIG. 6B vectors ρ1 (604) and ρ2 (605) define the relative locations of glints G1 (117) and G2 (118) with respect to the center C (112) of the object. Hereinafter the object center is assumed to be the instantaneous rotational point of the object. In a particular case of spherical or ellipsoidal objects, geometrical and rotational centers may coincide. However, there is no restriction of the shape of objects which can be tracked by various implementations of the present invention. Even convex object shapes are tractable.

An object to be tracked is characterized by the location of its center C (112) relative to coordinate origin K1 (103), as well as by its shape function $\rho(\theta,\phi)$ (606), which is essentially an equation defining the object surface (FIG. 6B). The shape function $\rho(\theta,\phi)$ defines the curvature $r(\theta,\phi)$ and normal vector $\tilde{n}(\theta,\phi)$ (603) at any point of the object surface.

The method of the present invention uses the following basic equations:

$$[\overline{e}_s \cdot \overline{n}_s] = \frac{[(\xi_s \overline{e}_s - \overline{A}_s) \cdot \overline{n}_s]}{\|\xi_s \overline{e}_s - \overline{A}_s\|}; s = 1, 2 \qquad (1)$$

As seen in FIG. 6A, vectors $\overline{A}_1$ (114) and $\overline{A}_2$ (115) are light source arms relative to origin K1 (103), whereas $\tilde{n}_1$ (601) and $\tilde{n}_2$ (602) are the normal vectors at glints G1 (117) and G2 (118), respectively.

For the first mode of operation the solution of equation system (1) is a pair of numbers $\xi_1$ and $\xi_2$, which are equal to the distances from glints (117) and (118) to camera K1 (103), respectively.

For the second mode of operation the solution of equation system (1) is a pair of numbers $\xi_1$ and $\xi_2$, which are equal to the distances from glints (118) and (204) to cameras K1 (103) and K2 (104), respectively.

The next step of the tracking procedure determines center location C (112), relative to coordinate origin K1 (103). The tracking of the object location is combined with a complete or partial determination of the object orientation, which can be implemented for two possible scenarios:

a) When the object shape is not spherical (i.e. $\rho(\theta,\phi) \neq const$). It should be noted that if the instantaneous point of rotation of a spherical object is different from its geometrical center, then for the purposes of tracking analysis such an object cannot be considered a spherical one.

b) If one or more marks are on the object surface (i.e. when the reflective coefficient depends on $(\theta,\phi)$).

Vectors $\overline{A}_1$ (114) and $\overline{A}_2$ (115) are used, together with function $\rho(\theta,\phi)$ (606), as input parameters in the method of the present invention. In addition, measurements of unit vectors $\tilde{e}_1$ (607) and $\tilde{e}_2$ (608) are taken in real time during the tracking process. Knowledge of their respective orientations enables the determination and tracking of a real-time object location and angular orientation.

B. Accuracy Estimation

To arrive at a rough estimate of accuracy achievable in practice, consider that a typical distance between adjacent pixels of a CCD video-chip is about 5 to 10 μm and that the focal length of a typical off-the-shelf camera is about 4 to 5 mm. Thus, the measurement error in determining vectors $\tilde{e}_1$ and $\tilde{e}_2$ is about $10^{-3}$ rad. For a 0.5 m distance between the object and camera, this translates into an accuracy of about 1 mm in determining the object location.

Optimization of component positioning (i.e. optimization of the relative positions of the camera and light sources) may be essential in increasing the measurement accuracy as well as improving the overall reliability of tracking. Optimum positioning is determined by the specific arrangement of a given optical tracking system.

Figure 7:
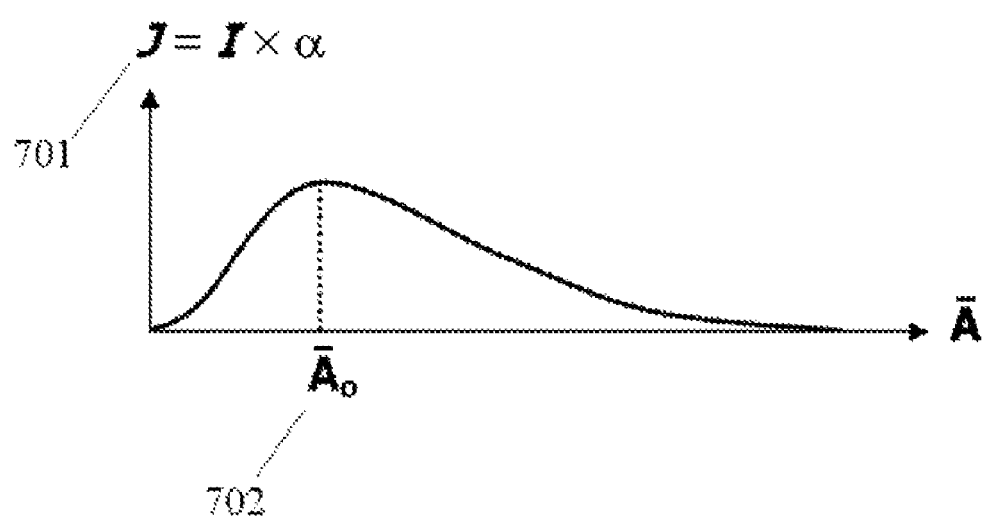
FIG. 7 shows the cost function J versus distance between the source and camera for the first operational mode.

General accuracy of the method is estimated here for the first operational mode, those skilled in the art will appreciate that the same evaluation can readily be extended to the second operational mode. Specifically, for the configuration shown in FIG. 6, the most important parameters for evaluation of tracking accuracy and reliability are the glint brightness I (intensity of the reflection from the light source) and the angle $\alpha$ between vectors $\tilde{e}_1$ and $\tilde{e}_2$. FIG. 7 schematically shows the dependence of the cost-function $J=I\times\alpha$ (701) versus the length of vector $\overline{A}$, i.e. source arm (114) or (115) (illustrated in FIG. 6A).

When the object size is significantly smaller than the distance between the source and camera (which is true for many practical applications), the optimum value of $\overline{A}_0$ (702) may be estimated as $$\overline{A}_0 \sim \sqrt{\frac{3}{2}} R, \tag{2}$$

where R (609) is the distance between the object center and the camera (origin), as shown in FIG. 6A.

In reality, two opposing cases are possible:

a) low glints brightness I (e.g. dim sources) and high resolution of the camera. In this case the optimum value of $\overline{A}$ may be less than $\overline{A}_0$ (702), which corresponds to a smaller angle $\alpha$ (119), see FIG. 1A, FIG. 6A.

b) high glints brightness I and low resolution of the camera. In this case the optimum $\overline{A}$ may be larger than $\overline{A}_0$ (702), which corresponds to a larger angle $\alpha$ (119), see FIG. 1A, FIG. 6A.

C. Tracking of Spherical Objects

The method described above in sections A and B may be applied to the tracking of spherical objects, as shown in FIG. 8. In this case, the equation system (1) can be rewritten in the form:

$$2R\,A_s\cos(\phi_s+x_s)=R^2+A_s^2-P_s^2-\rho^2-2P_s\,\rho\cos(y_s) \tag{3}$$

where:

$$y_s = \arcsin\left(\frac{R}{\rho}\sin(x_s)\right) \tag{4}$$

$$P_s = A_s \frac{\sin(\varphi_s)}{\sin(2y_s)} \tag{5}$$

and $$x_1+x_2+\phi_1+\phi_2=\pi \tag{6}$$

Figure 8A:
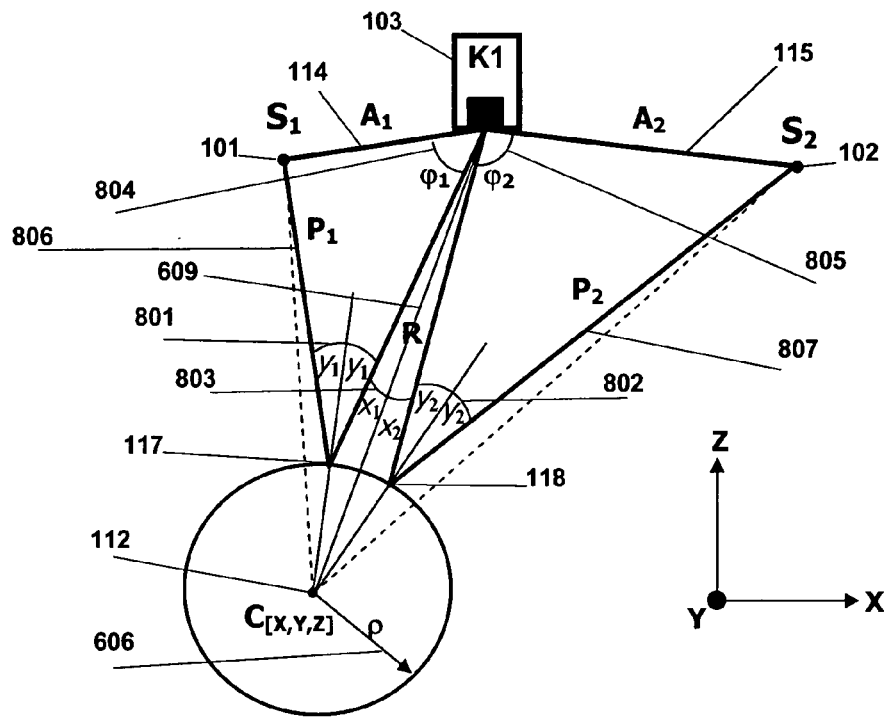
(FIG. 8A) a 2D view and a 3D model in an arbitrary reference frame (FIG. 8B).

Referring to FIG. 8A, $y_1$ and $y_2$ (801 and 802) are the incidence/reflection angle at glints (117) and (118), respectively. $P_1$ and $P_2$ (806 and 807) are the distances between the corresponding sources and glints. $\phi_1$ and $\phi_2$ (804 and 805) are the angles between the arms $A_1$ and $A_2$ (114 and 115) and the directions to the corresponding glints (117 and 118, respectively). $x_1$ and $x_2$ (803) are the angles between direction (103)-(112) (camera to sphere center) and the the directions to the corresponding glints (117 and 118, respectively).

Figure 8B:
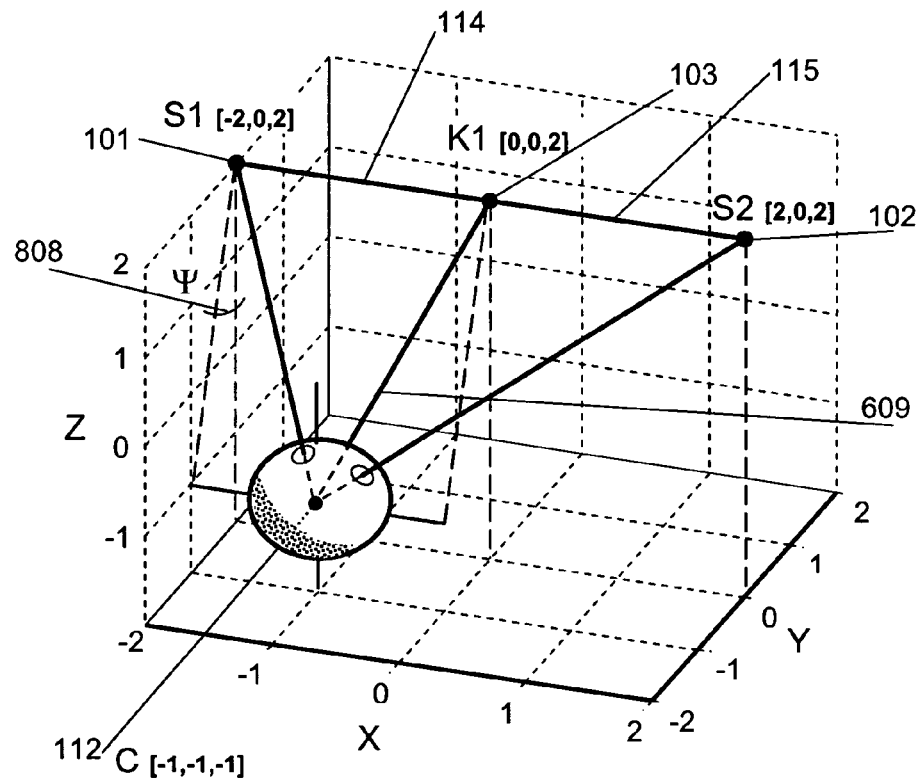
FIG. 8 illustrates the principle of spherical object tracking.

When tracking a spherical object, the input parameters for the algorithm are constant and known source arms $A_1$ and $A_2$ (114 and 115), the radius $\rho$ (606) of the object, as well as $\phi_1$ and $100_2$ (804 and 805). The latter change dynamically while tracking is performed. Since the object may be arbitrarily located at any spatial point (see FIG. 8B), the angle $\Psi$ (808) between plane ($S_1$ C $S_2$) ((101)-(112)-(102)) and plane (Z X) is introduced as an additional parameter to uniquely define the object position. The main output parameter of the algorithm is a 3-dimensional vector R (609), which is the solution of Eqs. (3)-(6) and uniquely determines the 3D position of the object center with respect to a stationary coordinate system (camera). FIG. 8B shows, by way of illustration but not limitation, a simplified case when the camera (coordinate origin) and two light sources are located on a straight line.

D. Tracking with Additional Degrees of Freedom

As presented in Section A, optical tracking with additional DoFs, i.e., with object rotational movements (yaw/pitch/roll), is possible for the two following cases when:

a non-spherical object has a shape known exactly or approximately;

the object surface has one or more marks of a known (or predictable) shape and a distinctive reflection coefficient.

The present invention is applicable to both these cases. Even though only the second case (object surface with marks) is described hereinafter by way of illustration, those skilled in the art will appreciate that the same method can be extended to tracking non-spherical objects.

5-DoF Tracking

For the simplest embodiment of the invention, consider a spherical object with a non-homogeneous reflection coefficient. For example, the object may have an elliptically shaped spot of a color (reflection coefficient) different from that of the rest of the surface. For relevance to eye tracking applications, a human eye was selected as a passive marker for 5-DoF optical tracking and is shown in FIG. 5B along with other optical markers (501). In this case, location and orientation measurements are performed with respect to the cornea sphere and used for gaze direction tracking.

The present invention can be applied to real-time 5-DoF eye tracking and readily be implemented for, and used in, computer applications whose goal is to determine a gaze direction and point-of-regard. Advantageously, the present invention inherently compensates for head movements.

6-DoF Tracking

The present invention can be extended to provide a complete 6-DoF tracking, i.e. when all three linear and three angular movements are present. It should be noted that the $6^{th}$ degree of freedom, which is roll movements, is not of much need for eye tracking applications. Compared to azimuth (yaw) and elevation (pitch) movements, roll movements are much less natural for the human eye, with possible exceptions being head rotation movements and small involuntary eye rolling movements. Nevertheless, there are some potential applications (e.g. contact lenses specially marked for 6-DoF tracking), for which the 6-DoF eye tracking capability may be useful.

In principle, any asymmetry in the object shape or surface reflection coefficient can be used to track roll movements, in addition to the azimuth and elevation tracking which may be performed as described above. It is desirable to implement the roll tracking capability as a straightforward extension of the present invention both in terms of its concept and experimental realization. Ideally, a single procedure for roll angle determination and extraction should be added, with little or none modifications needed for all the other 5-DoF tracking procedures. A horseshoe shaped mark, or, generally, a broken-ellipse-shaped mark (501) satisfies this condition and is thus used for 6-DoF optical tracking (FIG. 5A) in one preferred embodiment shown in. FIG. 5A also shows a simplified passive marker (113) which has a bright open-circle mark, optionally made of a retro-reflective material. The mark is positioned on a glass sphere (transparent) with the back (opposite) surface intentionally darkened. Advantageously, the bright mark and reduced scattering inside the sphere enable more robust image processing. In order to further reduce the influence of internal scattering within the sphere on the resulting image, the relative position of the sources with respect to the camera may be optimized. Specifically, in one preferred embodiment of the invention the light sources (101 and 102) and camera (103) are not located on a straight line.

E. Eye-Tracking

Figure 9:
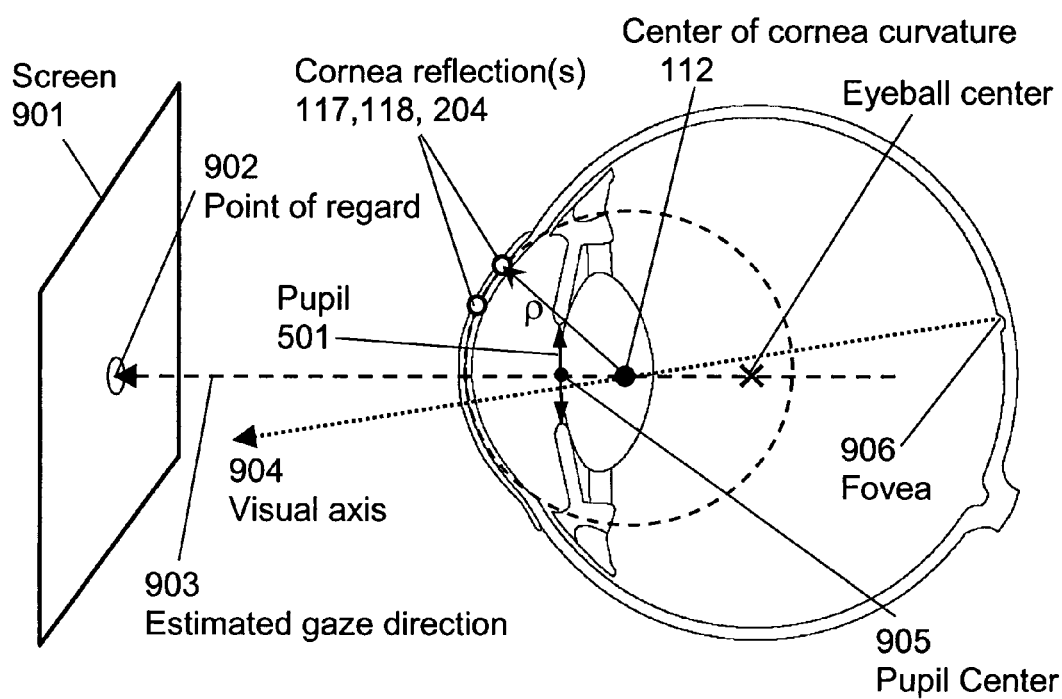
FIG. 9 shows a schematic of eye-gaze direction estimation. Gaze direction is derived from the images of the pupil and Purkinje reflections.

The present invention performs measurements of the eye-gaze direction by merging the disclosed optical tracking method for non-spherical objects with an eye-feature extraction technique. FIG. 9 schematically presents relationships between the eye features and gaze direction. The cornea is well approximated to be spherical. Therefore, the positions of glints (117), (118) and (204), which are the cornea reflections, do not change when the eye rotates, if the camera and light sources are stationary. In contrast, the pupil changes its position. The fovea (906) is the area of highest resolution on the retina, and the visual axis (904) is defined as the vector from fovea (906) to the center of the crystalline lens, as shown in FIG. 9. It is located about 2 mm (corresponding to about a 5 degree visual angle) to the temporal side of the central optic axis (903) which is the line through the center of the cornea and lens (pupil center). The diameter of the fovea corresponds to about a 1-degree visual angle. In other words, if a person looks at a disk with a diameter subtending a 1-degree visual angle, the image focused on the retina will cover an area about equal to that of the fovea.

In reality, the system estimates the gaze direction (903) from the center of cornea curvature (112) and the center of the pupil (905), rather than from the real visual axis. The estimated direction can then be easily corrected by a simple calibration as far as other types of errors (e.g. cornea curvature deviations and/or errors caused by head-movements) are pre-compensated.

F. Eye-Tracking Algorithm Structure

In one preferred embodiment of the invention, the algorithm performs two tasks:
image transformation for feature enhancement and preliminary detection of a possible position of a certain eye feature;
template matching in order to define eye-feature parameters.

Figure 10:
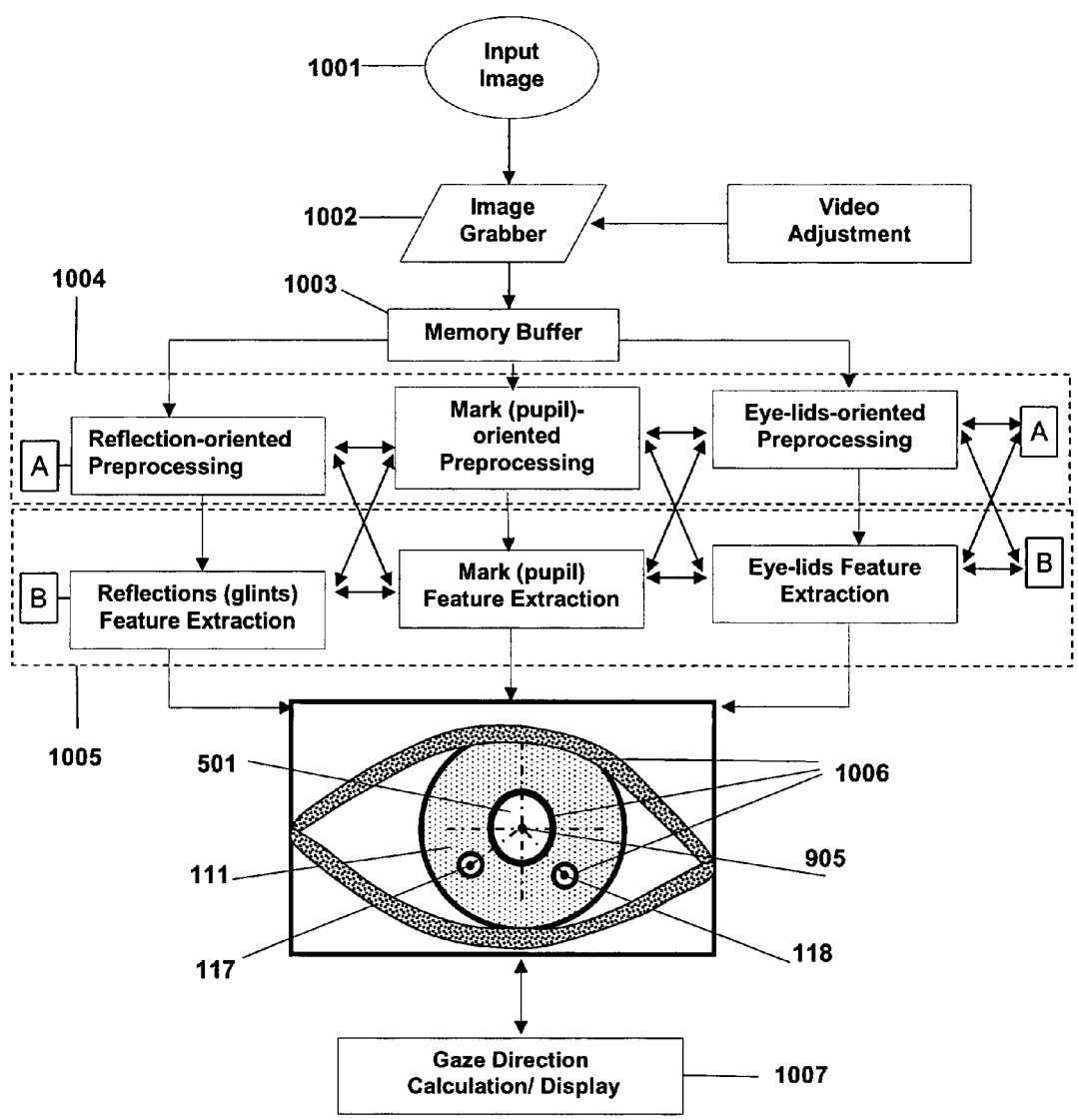
FIG. 10 shows a simplified top-level block diagram for eye tracking.

FIG. 10 shows a simplified block diagram of the basic eye tracking algorithm structure of image processing within the main program cycle of one preferred embodiment of the invention. At first, the video signal from the camera (1001) goes to an image grabber (1002) where the analog signal is converted into a digital stream and synchronization is recovered. From there, the digital pixels are passed on to a pre-processing module (1004). The pre-processing module performs a set of functions to support feature extraction. It includes numerically intensive operations, which are implemented in hardware and processed on the fly, while pixels arrive from the image grabber. The image pre-processing is done to accelerate feature extraction and includes numerically intensive operations. There are three possible independent information routes in the pre-processing—the pupil, CRs, and eyelids. Each includes sub-sampling, a correlator, and a center detection mechanism for the pupil and CRs. Sub-sampling downsizes the image to a manageable size and crops the image around an area with relevant information.

A memory buffer (1003) is used to transfer the pre-processing results to a DSP module. The pre-processing module includes many programmable sections, which are set by the DSP. The DSP performs the rest of the feature-extraction algorithm (1005). A multidirectional feedback (marked by bi-directional arrows in FIG. 10) to the pre-processing is used to set parameters to match the hardware implemented algorithms to changing eye conditions and environmental conditions.

Templates (1006) are preset using the expected features shape and used to guide the detection process. The sought features are the pupil, eyelids, and glints, i.e. cornea reflections (CRs). The algorithm finds template parameters that provide the best fit with the corresponding images. The fit is expressed by means of a cost function and the process uses the steepest decent strategy of this function. Variations of the template parameters should allow the template to fit the feature within any reasonable range of variation.

Some preliminary stages of the algorithm are used to locate an initial position of eye features and then deformable templates are used to extract and describe the eye features. Finally, the template deformation is applied to eye features tracking. Deformable templates (1006) are applied to three representations of the image (for the pupil, cornea reflection, and eyelids), as well as to the input image itself. These representations can be created by appropriate procedures, such as sub-sampling and application of a particular feature-enhancement-correlator.

The initial positions of the pupil and CRs centers, which may be different from the final values, are determined by pre-processing. Further processing is done to accurately estimate the pupil and CR centers (implemented in the DSP software). It is assumed that pre-processing, in combination with the interactions between different templates, will allow the templates to start relatively close to the exact position.

Finally, the inverse problem can be solved (1007) to compute the direction of gaze from the vectors connecting the center of the glints and the center of the pupil. The point of regard can also be computed from the intersection of the direction of gaze with an object in the scene.

Finally, the inverse problem can be solved (1007) to compute the direction of gaze from the vectors connecting the center of the object (eyeball) and the center of the pupil. The point of regard can be computed from the intersection of the direction of gaze with an object in the scene or screen.

Tracking accuracy changes in an inverse relationship with the distance between the cameras/sources and the object of regard (tracking range). For the second operational mode, accuracy deterioration over a wider tracking range may be compensated by increasing the distance between the cameras.

The disclosed apparatus has the following advantages: increased robustness and efficiency of eye tracking is achieved without additional cost;
unobtrusiveness to the operator, i.e. an eye-tracking device with no head-mounted gear and allowing for free head motion;
a simplified calibration procedure, which allows the 3-dimensional positioning of an object (e.g., a cornea sphere) to become an integral part of the method.

The foregoing description of a preferred embodiment of the invention has been presented for purposes of illustration and description. It is not intended to be exhaustive or to limit the invention to the precise form disclosed, and obviously many modifications and variations are possible in the light of the above teaching. The described embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A system for measuring a location and an orientation of an object of arbitrary curvature, comprising:
   a first and a second light sources illuminating the object;
   a first and a second cameras receiving a first and a second image of the object being illuminated by the light sources and providing a first and a second image data respectively; and
   a digital signal processing unit for receiving and analyzing the first and second image data for locating and tracking the object in real-time with six degrees of freedom, including rotational roll movement of the object around a vector from a coordinate origin to a center of the object, wherein
   a real-time measurement of 3-dimensional unit vectors $\{\bar{e}\}$ defines the directions between the first camera and glints from the respective sources is implemented accordingly to the system of equations:

$$[\bar{e}_s \cdot \bar{n}_s] = \frac{[(\xi_s \bar{e}_s - \bar{A}_s) \cdot \bar{n}_s]}{\|\xi_s \bar{e}_s - \bar{A}_s\|};$$

wherein s is the light source number, vectors A are distances between the first camera and corresponding light source, n are normal vectors at glints from the corresponded light sources and $\xi$ are distances from the first camera to the corresponded glints.

2. The system of claim 1, being adapted for tracking of a location and an orientation of an eyeball and optionally computing a direction of an eyeball gaze.

3. The system of claim 1, wherein the object has at least one mark on its surface, the mark being clearly recognizable on the first and the second images captured by the cameras and used for facilitating object motion tracking, the mark having uniform or non-uniform reflective coefficient across the surface.

4. The system of claim 3, wherein mark emits light.

5. The system of claim 1, wherein the system operates in a first and a second operational modes:
   the first operational mode uses the first camera to produce an image from the first and the second glints caused by the first and the second light sources, respectively;
   providing reliable and fast object locking, and
   the second operational mode involves the first and the second cameras to produce an image from the glint caused by the second light source only; providing more accurate object locking and tracking over larger tracking range and longer tracking distances compared to the first operational mode.

6. The system according to claim 5, further comprising a third camera located apart from the first and the second cameras, the third camera receiving a third image of the object and enabling the first and the second operational modes functioning independently and simultaneously:
   wherein the first operational mode uses the first camera to produce an image from the first and the second glints caused by the first and the second light sources, respectively;
   while the second operational mode, in parallel, involves the second and the third cameras to produce an image from the glint caused by the first light source only;
   providing more accurate object locking and tracking over larger tracking range and longer tracking distance compare to the first operational mode.

7. The system of claim 6, wherein the object has at least one mark on its surface, the mark being clearly recognizable on the first, the second and the third images captured by the cameras and used for facilitating object motion tracking, the mark having uniform or non-uniform reflective coefficient across the surface, and the mark optionally emits light.

8. The system according to claim 6, wherein at least one of the cameras has an additional light source, positioned coaxially with the camera, for emitting light toward the object.

9. The system according to claim 1, wherein the light sources emit light intermittently with a specified frequency and a sequence pattern.

10. The system of claim 9, wherein the first light source generates light with a state of polarization different from that of the second light source.

11. The system of claim 1, wherein the first and second cameras have discriminative sensitivity with respect to the first and the second light sources.

12. The system of claim 1, further comprising:
    a first and a second glints generated on the object's surface, the glints generated by reflection of the light from the first and second light sources respectively, wherein the first and the second image data include images of the glints.

13. The system of claim 1, wherein:
    the analyzing the first and the second image includes initial estimation of the object's three-dimensional location using the first image data outputted by the first camera.

14. The system of claim 1, further comprising:
    means for blocking the radiation from the first light source, and
    the digital signal processing (DSP) unit further performs receiving and analyzing the first and the second images of the object being illuminated with the second light source; the DSP unit measure and track a center of the object's three-dimensional location.

15. The system of claim 1, further comprising:
means for blocking the radiation from the first light source, the second image and a third image of the object being captured with the second camera and a third camera; and
the second and a third image data outputted by the second and the third cameras, respectively, the center of the object's three-dimensional location being determined and tracked by said second and the third image data.

16. The system of claim 1, further comprising:
the digital signal processing unit estimating an initial center of the object's three-dimensional location by the first image data outputted by the first camera;
means for blocking the radiation from the first light source;
the first and the second cameras performing a second acquisition of the first and the second images of the object, the object being illuminated with the second light source; and
the first and the second image data outputted by the first and the second cameras, respectively, the center of the object's three-dimensional location being precisely determined and tracked by the said first and a second image data.

17. The system of claim 1, further comprising:
a mark located on the object surface, its center location and direction being determined by the said first and the second image data;
the digital signal processing unit using the mark, the first and second image obtained by the first and the second cameras to determine the object's center three-dimensional location, orientation and three-dimensional unit vectors; the said object's center three-dimensional location being tracked with up to six degrees of freedom including pitch, yaw, and roll; and
a line of gaze being determined from the said three-dimensional location and orientation.

18. The system of claim 1, further comprising:
the digital signal processing unit using the first image data to determine the center of the object's three-dimensional initial location;
means for blocking the radiation from the first light source;
the second and the third cameras performing a second acquisition of the second and a third images of the object;
a second and a third image data outputted by the second and the third cameras, respectively,
the digital signal processing unit precisely determines and tracks the center of the object's three-dimensional location using the second and the third image data.

19. The system of claim 1, wherein
the first image data is processed by using preset parameters, the said parameters including a surface equation of the object and
a distance between the first light source and second light source,
a distance between the first camera and the second camera,
a distance between the first camera and the first light source,
a distance between the first camera and the second light source,
a distance between the second camera and the first light source and
a distance between the second camera and the second light source.

* * * * *